(12) United States Patent
Reed et al.

(10) Patent No.: US 9,050,199 B1
(45) Date of Patent: Jun. 9, 2015

(54) TRANSFEMORAL PROSTHESES HAVING ALTERED KNEE LOCATIONS

(71) Applicants: Kyle B. Reed, Tampa, FL (US); John R. Sushko, Tampa, FL (US); Craig A. Honeycutt, Holiday, FL (US)

(72) Inventors: Kyle B. Reed, Tampa, FL (US); John R. Sushko, Tampa, FL (US); Craig A. Honeycutt, Holiday, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 13/864,714

(22) Filed: Apr. 17, 2013

Related U.S. Application Data

(60) Provisional application No. 61/625,400, filed on Apr. 17, 2012, provisional application No. 61/723,046, filed on Nov. 6, 2012.

(51) Int. Cl.
*A61F 2/62* (2006.01)
*A61F 2/64* (2006.01)

(52) U.S. Cl.
CPC ........................................ *A61F 2/64* (2013.01)

(58) Field of Classification Search
CPC .......................................................... A61F 2/64
USPC .......................................................... 623/39
See application file for complete search history.

(56) References Cited

U.S. PATENT DOCUMENTS

| 3,400,408 | A | * | 9/1968 | Garcia | ............................ 623/43 |
| 8,057,550 | B2 | | 11/2011 | Clausen | |
| 2009/0265018 | A1 | | 10/2009 | Goldfarb | |

OTHER PUBLICATIONS

Anthony Staros, "Dynamic Alignment of Artifical Legs with the Adjustable Coupling", Digital Resource Foundation for Orthotics & Prosthetics Community, 1963, vol. 7, No. 1.
Oaao Bock, Quality for Life, C-Leg® Technology, Advanced Prosthetic Knee Technology, Family of Products, 2011 Otto Bock Healthcare.
Torrealba, et al. "Through the Development of a Biomechantronic Knee Prosthesis for Transfermoral Amputees: Mechanical Design and Manufacture, Human Gait Characterization, Intelligent Control Strategies and Tests", 2010 IEEE International Conference on Robotics and Automation, May 3-8, 2010.
Honeycutt, et al. "Asymmetric Passive Dynamic Walker", Jun. 20, 2011, IEEE International Conference on Rehabilitation Robotics.
John Sushko, "Asymmetric Passive Dynamic Walker Used to Examine Gait Rehabilitation Methods", Oct. 2011.
Craig Honeycutt, "Utilizing a Computational Model for the Design of a Passive Dynamic Walker", Oct. 2011.
Sushko, et al. "Implications for Prosthesis Design Based on an Asymmetric Passive Dynamic Walker", 2012.

* cited by examiner

*Primary Examiner* — Jacqueline Woznicki
(74) *Attorney, Agent, or Firm* — Thomas | Horstemeyer, LLP

(57) ABSTRACT

In one embodiment, a prosthesis includes an upper portion adapted to interface with a user's leg, a lower portion adapted to interface with a floor or ground surface, and a knee joint that pivotally connects the lower portion to the upper portion, wherein the knee joint is physically displaced from the user's natural knee line along the leg.

14 Claims, 10 Drawing Sheets

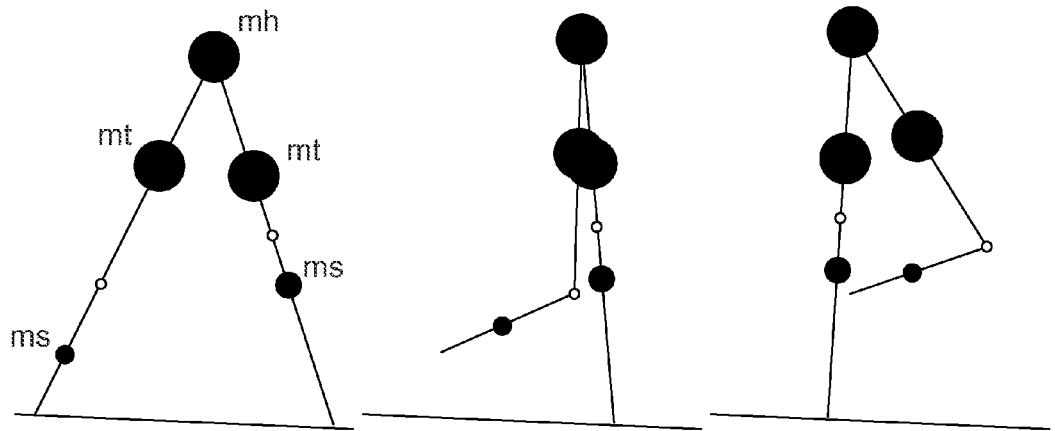
FIG. 7A  FIG. 7B  FIG. 7C
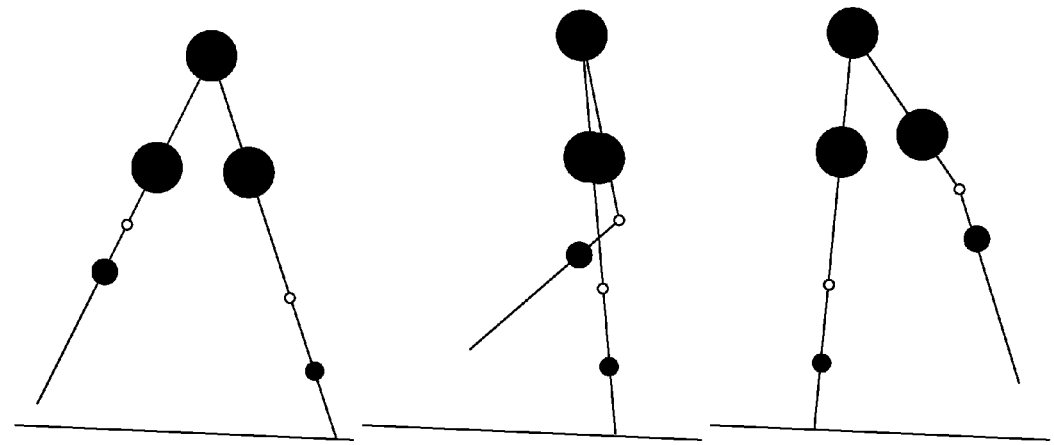
FIG. 7D  FIG. 7E  FIG. 7F

TRANSFEMORAL PROSTHESES HAVING ALTERED KNEE LOCATIONS

CROSS-REFERENCE TO RELATED APPLICATIONS

This application claims priority to U.S. Provisional Application Ser. No. 61/625,400, filed Apr. 17, 2012, and U.S. Provisional Application Ser. No. 61/723,046, filed Nov. 6, 2012, both of which are hereby incorporated by reference herein in their entireties.

BACKGROUND

Typical transfemoral prostheses comprise a femoral portion that replaces the missing portion of the patient's thigh and a tibial portion that replaces the patient's lower leg. The two portions of the prosthetic are joined by a "knee" joint that, when the prosthetic is worn, aligns with the location at which his or her knee previously existed.

While such prostheses are of great benefit to transfemoral amputees, they often are not ideal. Specifically, such amputees often have an asymmetric gait when using conventional transfemoral prostheses. It can therefore be appreciated that it would be desirable to have a transfemoral prosthesis that enables transfemoral amputees to have a more symmetric gait.

BRIEF DESCRIPTION OF THE DRAWINGS

The present disclosure may be better understood with reference to the following figures. Matching reference numerals designate corresponding parts throughout the figures, which are not necessarily drawn to scale.

FIGS. 7A-7F illustrate different stages of walking with a transfemoral prosthesis of the type illustrated in FIG. 1.

DETAILED DESCRIPTION

As described above, it would be desirable to have a transfemoral prosthesis that enables transfemoral amputees to have a more symmetric gait. As described herein, physical asymmetries can be used in the design of transfemoral prostheses to improve the gait of such persons. More particularly, a prosthetic leg design can be used in which the knee location is shifted from the natural knee line. In such a case, overall prosthetic mass can be decreased, especially below the knee. A lighter prosthetic that enables a symmetric gait increases comfort and decreases the detrimental effects of an asymmetric gait. In some embodiments, the knee joint of the prosthesis is positioned below the natural knee line. This physical asymmetry results in both below-knee mass reduction and total mass reduction, while enabling a more symmetric gait.

In the following disclosure, various specific embodiments are described. It is to be understood that those embodiments are example implementations of the disclosed inventions and that alternative embodiments are possible. All such embodiments are intended to fall within the scope of this disclosure.

This disclosure extends the past and current mathematical models of passive dynamic walkers (PDWs) to introduce a corporeal example of how they can be used for rehabilitation and prosthetic designs. This disclosure further describes how the rotational inertia and the center of gravity of each extremity relate to step-length patterns. A practical application of the model suggests a deviation from typical prosthetic designs in the form of shifting the position of the knee to a location dissimilar to the natural leg.

Figure 1:
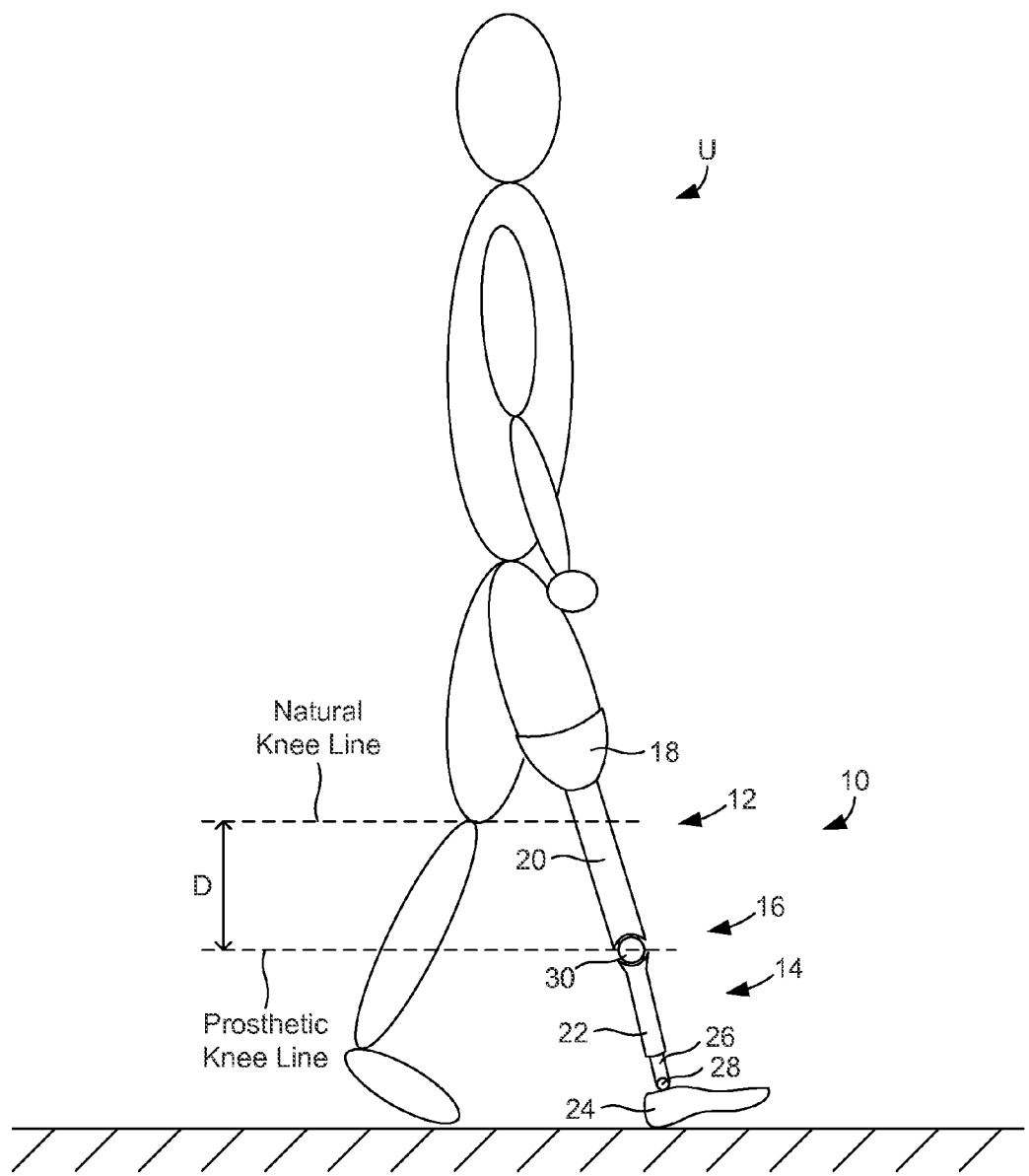
FIG. 1 is a side view of a first embodiment of a transfemoral prosthesis worn by an amputee user.

FIG. 1 illustrates an example transfemoral prosthesis 10 that is worn by an amputee user U. The user U is a transfemoral amputee, meaning that the user's lower leg, knee, and a portion of the upper leg have been amputated. In the example of FIG. 1, approximately a third of the user's right thigh (and femur) has been removed. The prosthesis 10 generally comprises an upper portion 12 adapted to interface with the user's leg, a lower portion 14 adapted to interface with a floor or ground surface, and a "knee" joint 16 that pivotally connects the lower portion to the upper portion. In the illustrated embodiment, the upper portion 12 includes a thigh interface 18 and a shaft 20 that extends downward from the thigh interface. The thigh interface 18 can be a cup-shaped member that is adapted to receive and attach to the remaining portion of the user's thigh (i.e., the "stump"). The shaft 20 of the upper portion 12 of the prosthesis can be an elongated hollow tube. In some embodiments, the shaft 20 is made of a strong, lightweight material such as aluminum or titanium. Because it replaces a part of the missing thigh and femur, the upper portion 12 of the prosthesis 10 can be referred to as the thigh or femoral portion of the prosthesis.

The lower portion 14 of the transfemoral prosthesis 10 includes an elongated shaft 22 and a foot prosthesis 24. In the illustrated embodiment, the foot prosthesis 24 is connected to the shaft 22 with another shaft 26 that includes a joint 28 that enables the foot prosthesis to pivot relative to the shaft 26. In some embodiments, the shafts 22, 26 and the foot prosthesis 24 are made of a strong, lightweight material such as aluminum or titanium. Because it replaces the missing shin and tibia, the lower portion 14 of the prosthesis 10 can be referred to as the shin or tibial portion of the prosthesis.

As mentioned above, the lower portion 14 of the transfemoral prosthesis 10 is pivotally connected to the upper portion 12 of the prosthesis with the knee joint 16. In some embodiments, the knee joint 16 comprises a simple hinge 30 that enables pivoting of the lower portion 14 about a single axis. Irrespective of the nature of the joint 16, it is physically displaced from the user's natural knee line. As used herein, the term "natural knee line" refers to the position or height at which the user's amputated knee previously lied when the user was standing. In cases such as that illustrated in FIG. 1 in which the user is a single-leg transfemoral amputee, the natural knee line coincides with the position or height of the user's remaining knee (see figure). The knee joint 16 can be displaced along the length of the user's prosthetically-augmented leg so as to be positioned above or below the natural knee line. In the example of FIG. 1, the knee joint 16 is positioned below the natural knee line so as to reduce the length and weight of the lower portion 14 of the prosthesis 10. In some embodiments, the center (i.e., the pivot axis) of the knee joint 16 is shifted downward from the natural knee line a distance that is approximately 10 to 60% of the length of the user's missing (or intact) lower leg (including the foot). For example, the center of the knee joint 16 can be shifted downward from the natural knee line a distance that is approximately 20 to 50% or 30 to 40% of the length of the missing (or intact) lower leg. In most amputee users, this means that the center of the knee joint 16 is positioned approximately 3 to 7 inches below the natural knee line and therefore approximately 3 to 7 inches lower than the position of the user's remaining knee in the case of single-leg amputees. This distance is represented by D in FIG. 1. As shown in that figure, the distance D is the distance between the natural knee line and the prosthetic knee line.

In practice, the transfemoral prostheses 10 can be produced so that one or more predetermined knee joint positions are provided for each size of prosthesis. As an example, the prostheses 10 can be produced in three variants, a first in which the knee joint is shifted downward a distance equivalent to approximately 25% of the length of the missing lower leg, a second in which the knee joint is shifted downward a distance equivalent to approximately 35% of the length of the missing lower leg, and a third in which the knee joint is shifted downward a distance equivalent to approximately 45% of the length of the missing lower leg. It can then be determined which knee joint position is most appropriate for the particular amputee to whom the prosthesis is to be provided. Once that determination has been made, the amputee can be fitted with an appropriately sized transfemoral prosthesis and his or her gait can be evaluated to determine the most appropriate mass for the upper shaft and the lower shaft and the particular locations of those masses in order to achieve an even gait. The appropriate masses can then be added to the prosthesis in the appropriate places, for example, by affixing weights to discrete locations on the prosthesis, and the amputee can be encouraged to try the prosthesis for a brief time period (e.g., a few weeks) to test it. The amputee can then return for a follow-up evaluation and adjustments can be made, if necessary.

To validate the possibilities of a prosthesis with physical asymmetries relative to the amputee's unaltered leg, the effects of moving the rotational inertia without changing the center of mass were investigated. A PDW model was used because of its similarity to human gait. Also, because purely dynamic effects are being investigated, a model excluding human cognition was desired. To better explore the effects of changing the center of mass and moment of inertia of each leg independently, a nine-mass model was considered. This model increases the number of masses typically considered to better describe the distribution of mass throughout the limb. Also, while conventional five-mass models only account for the center of mass of each extremity, the nine-mass model can more accurately represent inertia.

The PDW model divides the gait cycle into four discrete phases. These are the three-link phase, the two-link phase, knee strike, and heel strike. For a successful gait to be established, the energy lost at knee strike and heel strike (i.e., the collision events) is gained from gravity's effect on the overall inertia of the mechanism. The gait cycle has been compared to a rimless wheel with collisions occurring as each spoke makes contact with the ground. Expanding on this concept is the compass gait model, which is fundamentally a double pendulum with a hip mass and two leg masses. This concept was expanded by creating a five-mass system to more accurately describe a PDW with knees. In a previous model, masses were specified in terms of which leg they were associated with, providing one with the ability to make physical asymmetries within the model.

The effects of modifying physical parameters in the PDW model were observed by moving the location of the knee, manipulating the location and magnitude of the masses, and changing the overall length of each leg. In doing this, several different step patterns were identified that could relate to gait irregularities in humans. The model was then tuned with physical asymmetries to observe the resulting walking patterns.

The discussion below explores the effects of changing masses and mass locations while directly applying these changes to a practical application. A nine-mass model having an asymmetric step pattern is first presented and is then tuned towards symmetry. Then, the prosthesis is analyzed using the nine-mass model.

Figure 2:
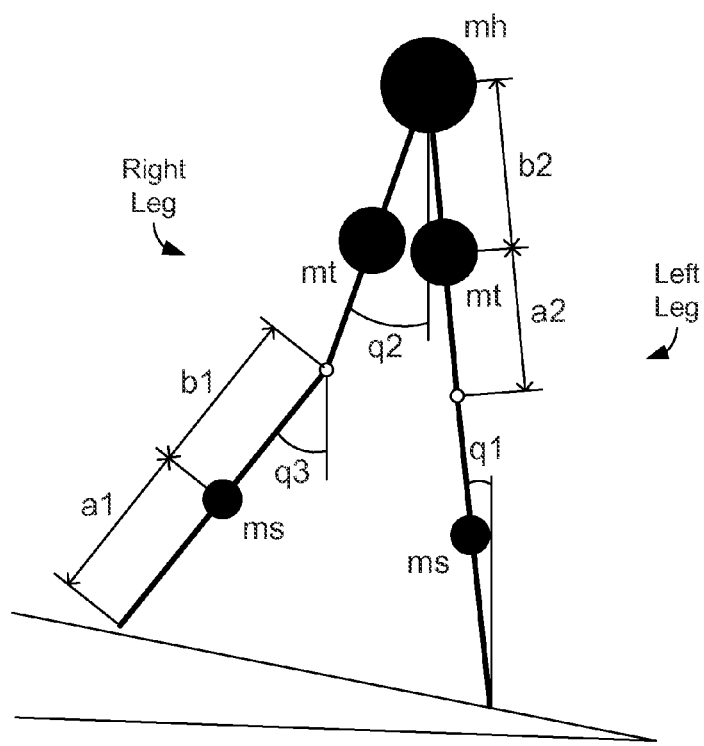
FIG. 2 is a schematic diagram of a five-mass walker model that can be used to simulate human walking.
Figure 3:
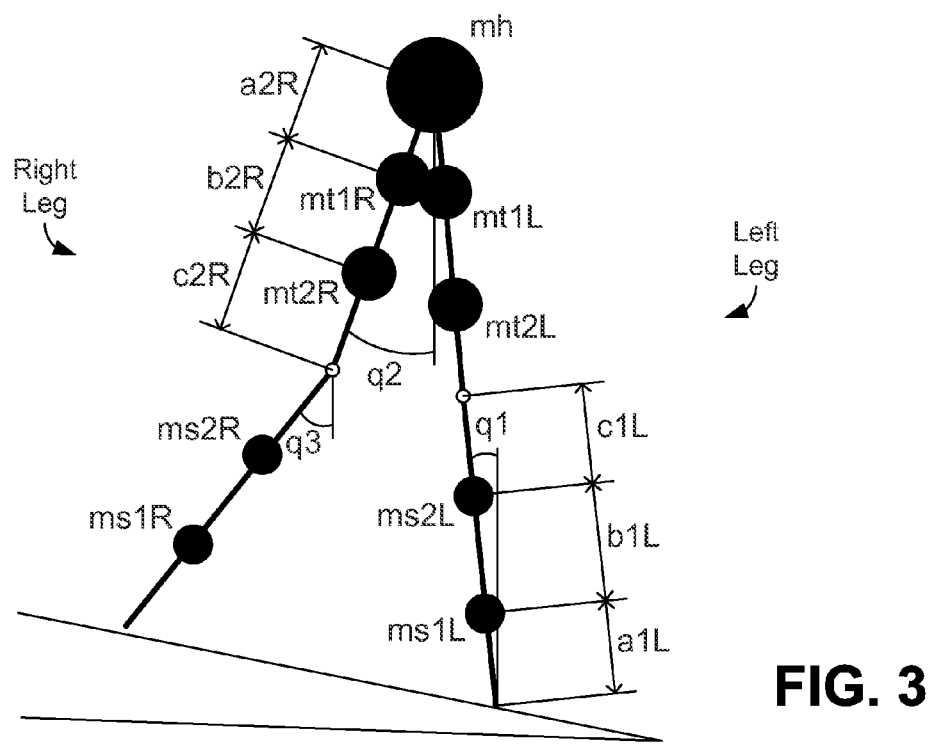
FIG. 3 is a schematic diagram of a nine-mass walker model that can be used to simulate human walking.

A kneed passive dynamic walker can be modeled as an unactuated multi-pendulum system. In an early kneed model, knees and shanks were added to the compass gait system to better describe the human gait. This model has a total of five masses. In order to differentiate the legs, the following needs to be established: the stance leg (st) is the leg that is in contact with the ground and the swing leg (sw) is the leg that swings freely. The five-mass model can be seen in FIG. 2. As shown in that figure, the model includes a hip mass (mh), two thigh masses (mt), and two shin or shank masses (ms). One-dimensional tests were performed to evaluate the effects of independently changing the mass of the right shank, the location of the thigh mass, and the location of the knee. This provided interesting gait patterns and a basis of how the parameters affect step patterns. The model was then further advanced by adding a mass on each link. Four additional masses were introduced bringing the total to nine. The nine-mass system is shown in FIG. 3. A major benefit of the nine-mass system is that the mass distribution of human legs and the legs of a physical PDW can be better approximated, which aids in the development of different rehabilitation methods. The nine-mass system also provides a large amount of adjustability and versatility for different model configurations.

The nine masses shown in FIG. 3 include the hip mass (mh), two right thigh masses (mt1R, mt2R), two right shank masses (ms1R, ms2R), two left thigh masses (mt1L, mt2L), and two left shank masses (ms1L, ms2L). The thigh and shank masses can be alternatively designated as being on the stance leg (st) or the swing leg (sw). In such a case, the nine-mass model can be considered to include the hip mass (mh), the upper shank mass on the stance leg ($ms2_{st}$), the lower shank mass on the stance leg ($ms1_{st}$), the upper thigh mass on the stance leg ($mt1_{st}$), the lower thigh mass on the stance leg ($mt2_{st}$), the upper shank mass on the swing leg ($ms2_{sw}$), the lower shank mass on the swing leg ($ms1_{sw}$), the upper thigh mass on the swing leg ($mt1_{sw}$), and the lower thigh mass on the swing leg ($mt2_{sw}$). The bottom rods are the shank links and the top rods are the thigh links. The shank length is ls=a1+b1+c1 and the thigh length is lt=a2+b2+c2, both in terms of st and sw. The total length is L=ls+lt, also in terms of st and sw. The walker goes through two distinct stages in its gait pattern: a two-link phase and a three-link phase. The walker starts in the three-link phase in which it acts as a three link pendulum system. The three-link phase, shown in FIG. 3, is described as $L_{st}$ which is connected by the hip to $lt_{sw}$ and the knee connects $lt_{sw}$ to $ls_{sw}$. The walker stays in the three-link phase until the knee strike collision occurs. After knee strike, the knee is locked and the system becomes a double pendulum. The double pendulum system is the two-link phase (not shown). The two-link phase has two links $L_{st}$ and $L_{sw}$, which are connected together by the hip. The walker stays in the two-link phase until the heel strike collision. The heel strike finishes the walker cycle and the three-link phase starts the cycle again. The nine-mass system's dynamics can be described by the Lagrangian formulation for a multi-pendulum system shown in Equation 1, $$H(q)\ddot{q}+B(q,\dot{q})\dot{q}+G(q)=0 \qquad \text{Equation 1}$$

where the three matrices H, B, and G are the inertia, velocity, and gravity matrices, respectively. The nine-mass model is essentially the five-mass model with added terms in the Lagrangian matrices. Equation 2 shows the first term in the inertia matrix for the five-mass system, $$H_{11} = ms_{st}a1_{st}^2 + mt_{st}(ls_{st}+a2_{st})^2 + (mh+ms_{sw}+m_{sw})L_{st}^2, \qquad \text{Equation 2}$$

and Equation 3 is the first term for the nine-mass system, $$H_{11} = ms1_{st}a1_{st}^2 + ms2_{st}(a1_{st}+b1_{st})^2 + \qquad \text{Equation 3}$$
$$mt2_{st}(ls_{st}+c2_{st})^2 + mt1_{st}(ls_{st}+c2_{st}+b2_{st})^2 +$$
$$(mh+ms1_{sw}+ms2_{sw}+mt1_{sw}+mt2_{sw})L_{st}^2$$

While the nine-mass system was derived to make the model more versatile, the question remains whether the extra masses make a significant difference. To determine this, only the moment of inertia on specific links on the right leg were changed, while keeping the center of mass constant. The two masses move an equal distance away from the baseline location. The parameter that separates the two masses on each link for the right leg was incremented from 0 meters (m) to 0.5 m (i.e., b1R and b2R). There were three tests performed by incrementing b1R and b2R separately, and both b1R and b2R simultaneously, with the goal of finding the value of these parameters that produced the largest asymmetry but with the model still able to walk stably.

Figure 4A:
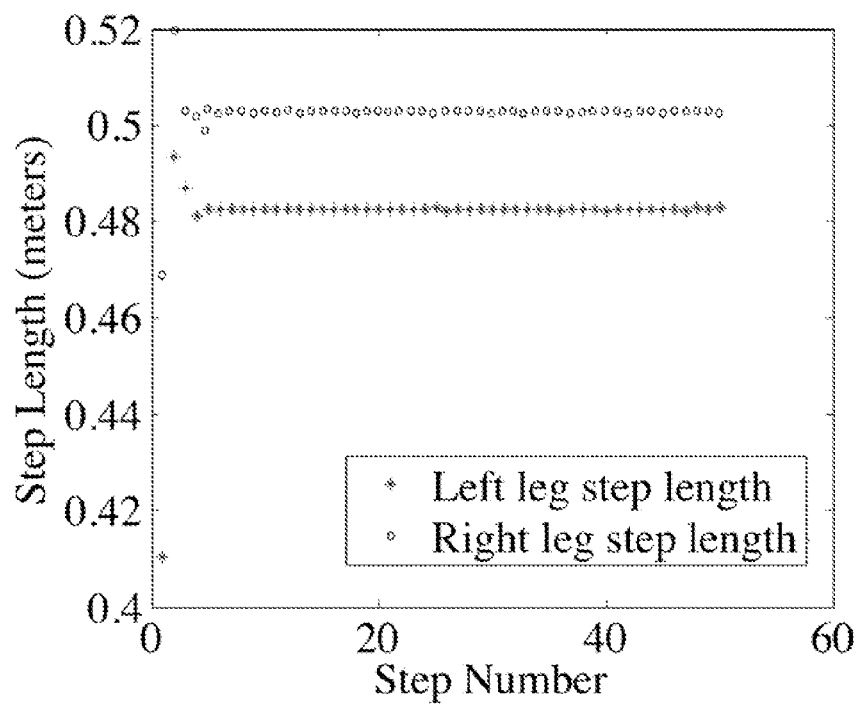
FIGS. 4A-4C are step-length plots that illustrate an asymmetry that arises because of the altered moment of inertia when two masses on the thigh and/or shank of the nine-mass walker model are separated.
Figure 4C:
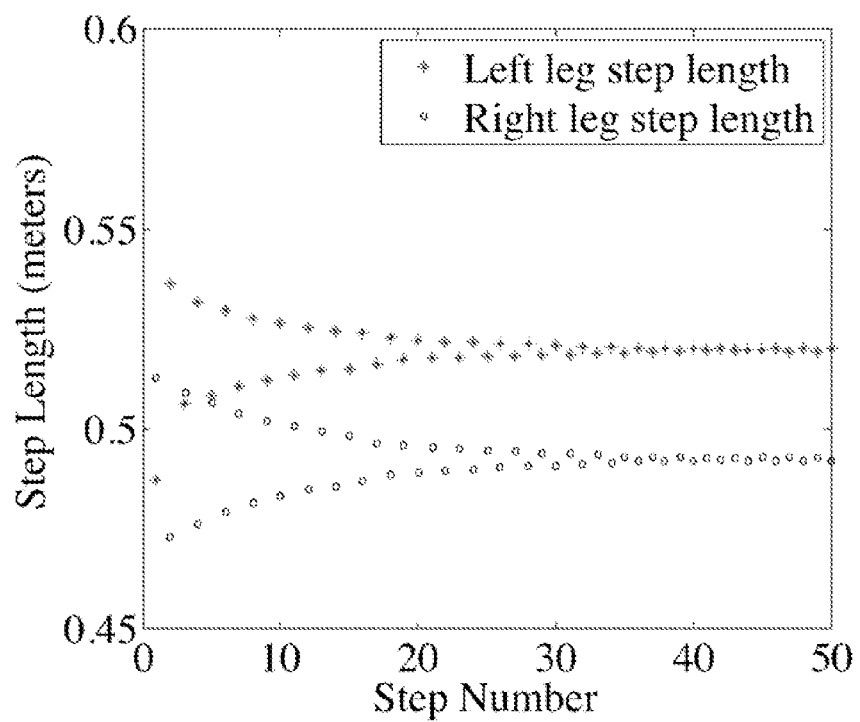
Figure 4B:
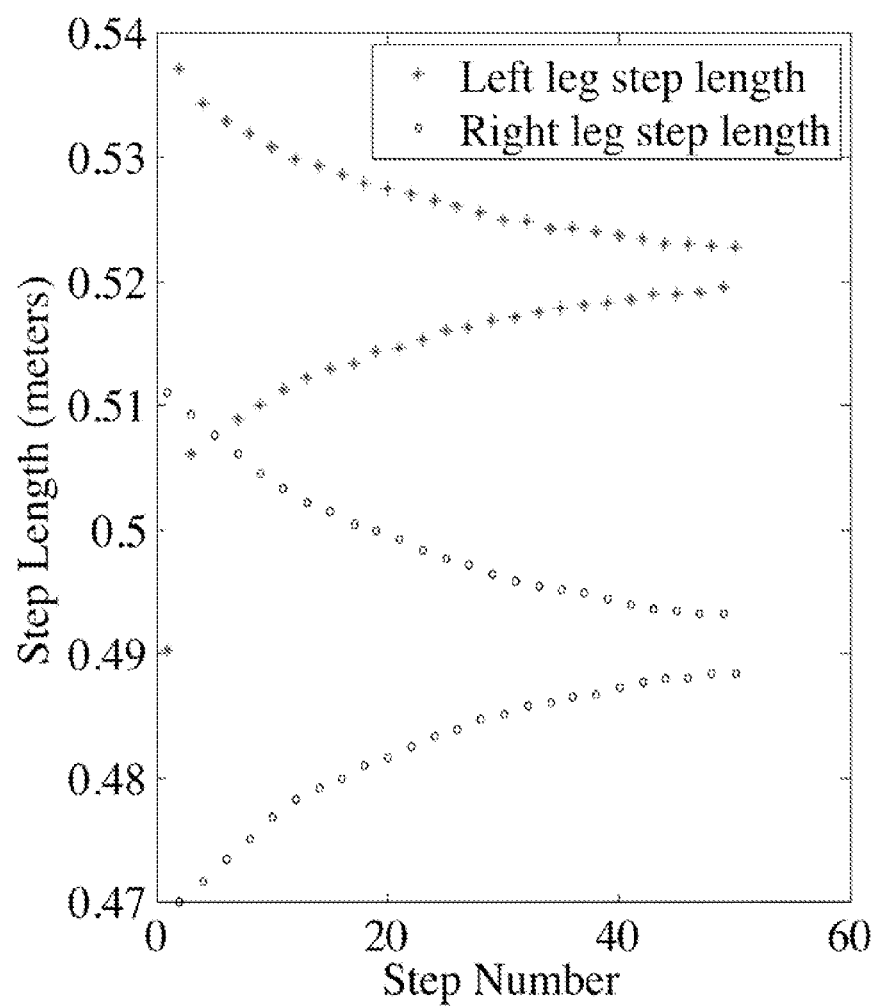

For a test to be considered successful, the walker had to walk for 50 steps. The largest asymmetry for the shank is 0.0212 m, which occurs when the two masses are separated by b1R=0.24 m, which is shown in the step-length plot of FIG. 4A. When the two thigh masses are separated by a distance b2R=0.25 m, the system produces a step length difference of 0.0297 m, shown in FIG. 4B. The combined thigh and shank test produced an asymmetry of 0.029 m when the shank masses are separated by b1R=0.03 m and the thigh masses by b2R=0.26 m, shown in FIG. 4C. These results show that the moment of inertia alone can substantially influence the gait pattern. Note that all of these asymmetries arise from changing the moment of inertia on the right leg only while keeping the left leg parameters constant.

Next, the configurations with the largest asymmetries arising from changing the right leg only were used as a baseline to test the effect of shifting the center of mass location on the left leg shank and thigh. In other words, the center of mass was changed on the leg opposite from the leg on which the moment of inertia was changed. This test determines if the asymmetry can be eliminated by changing the center of mass on the left leg. The two masses on the left leg segments were located at the same location by setting b1L and b2L to zero. Essentially two large masses were used, one on the shank and one on the thigh. Note that the center of mass and the moment of inertia of the left leg are coupled while the location of the one larger mass is moved. This is unlike the right leg where the center of mass stays the same and the moment of inertia varies.

Figure 5A:
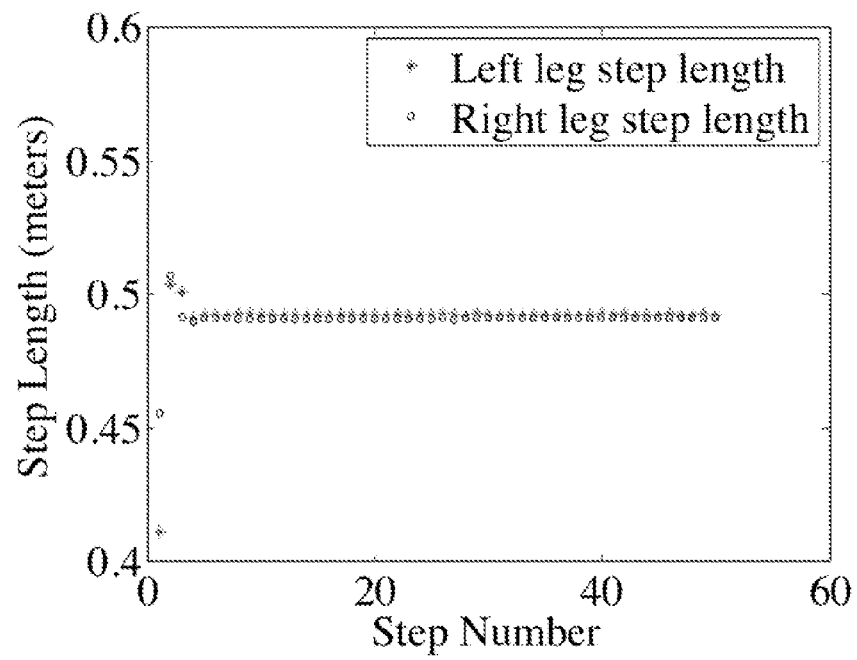
FIGS. 5A-5C are step-length plots that illustrate symmetric gaits generated by altering only the masses of the left leg of the nine-mass walker model.
Figure 5B:
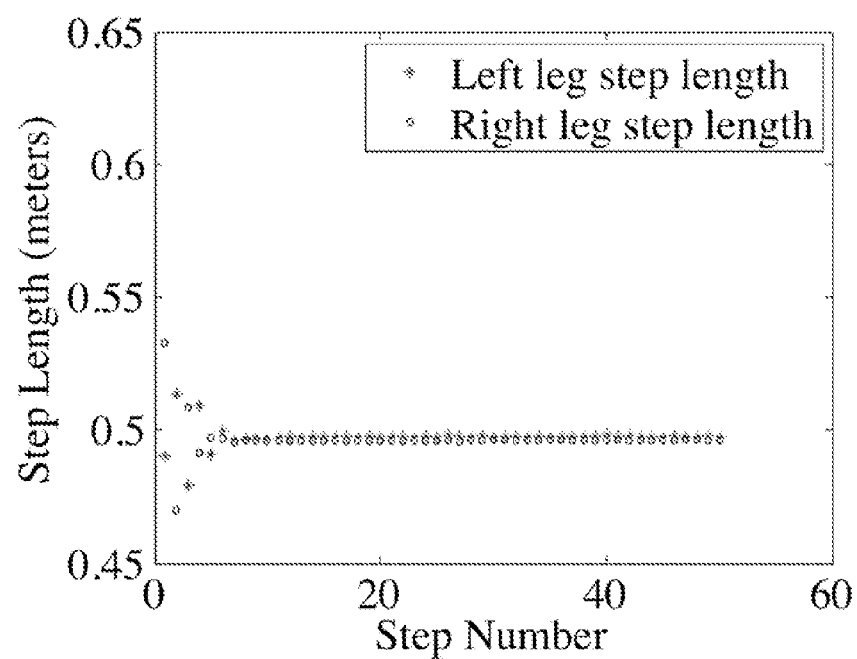
Figure 5C:
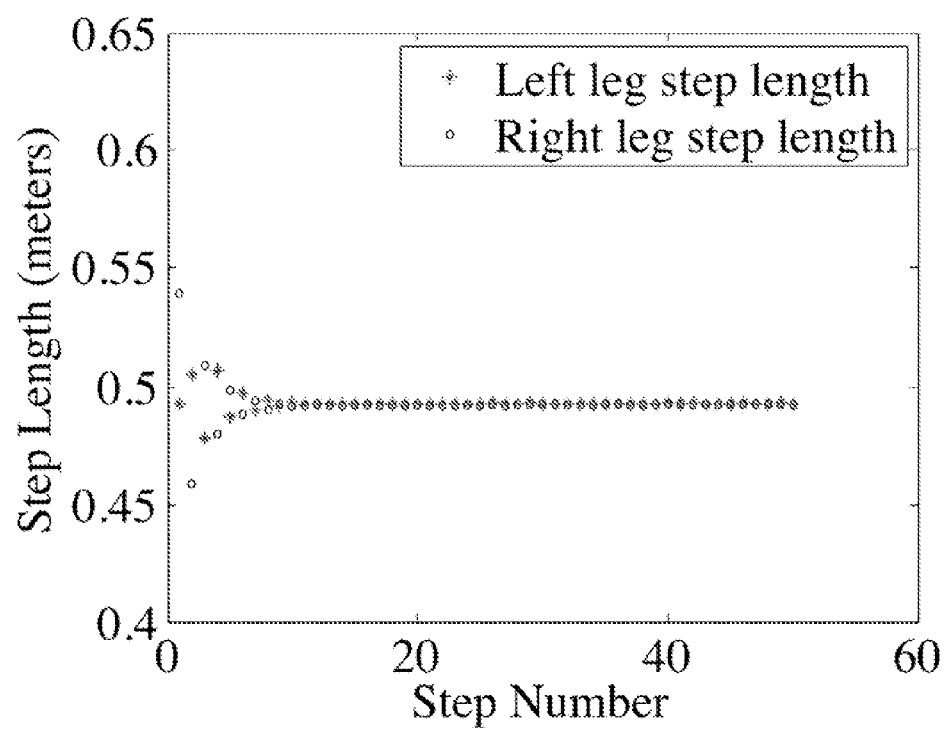

The values of c1L and a2L were independently iterated from 0 m to 0.5 m with all permutations evaluated by a brute force search. The values of a1L and c2L were modified in each case to maintain the same total shank and total thigh lengths. There are certain parameters that lead to a symmetric gait pattern when the center of mass is moved along both the shank and the thigh. In FIG. 5 it can be seen that the walker can return to symmetry when the masses on the left leg are at a specific location. These are the step length plots which plot the step length vs. the step number. FIG. 5A shows the symmetric solution to the asymmetry created in FIG. 4A, which is the asymmetry that arises when the masses on the right shank are spread out by 0.24 m. This created asymmetry is canceled out when the large coupled masses on the left leg shank and thigh are both moved to 0.01 m above the center of the shank and thigh links, respectively. FIG. 5B shows the diminished asymmetry initially caused by the right leg thigh masses being separated by 0.25 m. The reduction happens when the coupled masses on the left leg shank are moved to 0.17 m below the knee and the thigh mass is in the center of the thigh link (i.e., a2L=0.25 m). In view of FIG. 5C, it can be seen that the asymmetry in FIG. 4C was eliminated when the shank and thigh masses were moved to 0.14 m below the knee and 0.23 m below the hip. This shows that with a specified center of mass and moment of inertia for one leg, the walker can be tuned to symmetry by holding the center of mass constant and varying the moment of inertia of the opposite leg.

Figure 6:
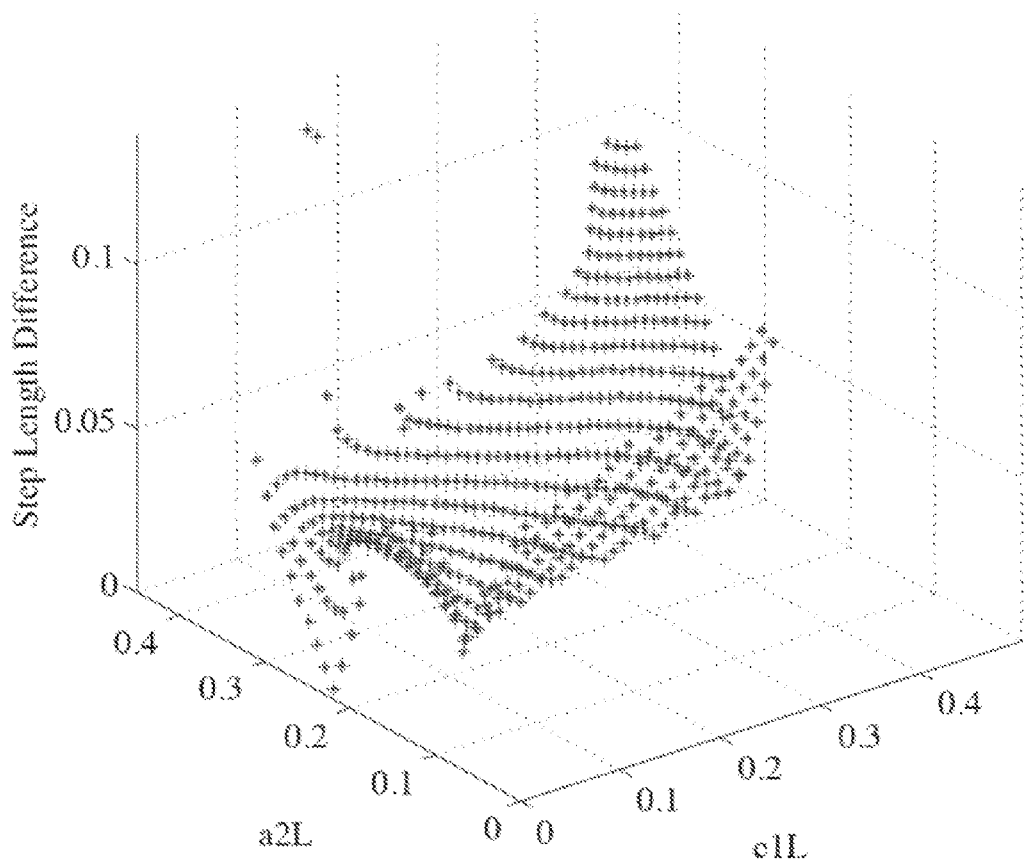
FIG. 6 is a three-dimensional plot of the distance a2L versus the distance c1L versus step length difference.

Also of interest is how the step length difference changes as the moment of inertia changes. Using the data from the test when b2R is 0.25 m, c1L and a2L were each iterated from 0 m to 0.5 m. The moment of inertia for each leg was then plotted versus the step length difference. As shown in FIG. 6, which is a three dimensional plot of a1L versus c2L versus step length difference, the moment of inertia of the left leg is dependent upon the location of the mass. The location of the shank and thigh masses on the left leg changes with c1L and a2L. When c1L is approximately 0.3 m, the walker will be more stable. However, if a2L is too large, the step length difference will increase making the walker more unstable. This can also be seen in FIG. 6, which shows that there is a range of values of c1L and a2L that produce a symmetric walker given an altered moment of inertia on the opposite leg. Because of this, there would be many solutions to an optimization problem based solely on step symmetry. Several specific configurations were manually selected to highlight in the following results.

For prosthesis tests, the nine-mass model should be modified to be as anatomically correct as possible. An anthropomorphic model was used to accomplish this, which gave the location and magnitude of the center of mass for each part of the leg. Those values were taken and allowed to vary slightly until a stable and symmetric gait pattern was generated. The values of the parameters for the anthropomorphic model are listed in Tables I and II. Then, to develop a model for the prosthesis, an amputation point of two thirds of the total thigh length distally from the hip was assumed. Different knee locations and masses of the prosthetic thigh and shank were then iterated through until symmetry in the gait was obtained. FIGS. 7A-7F show the mass distribution of both the intact and prosthetic legs at different stages of walking with a transfemoral prosthesis of the type illustrated in FIG. 1. For the intact leg, both thigh masses were placed at the center of mass given by the anthropomorphic model and each were given a value that is one half of the total thigh mass, simulating a single mass. One shank mass was used for the center of mass of the shank and the other was moved down to represent the foot's center of mass. A similar distribution was used for the prosthetic leg with the exception of the thigh masses. Here, one thigh mass was used to represent the center of mass of the stump while the other was used for the center of mass of the prosthetic thigh.

TABLE I

Anthropomorphic Model Mass

|  | Mass of hip (kg) | Mass of thigh (kg) | Mass of shank (kg) | Mass of foot (kg) |
| --- | --- | --- | --- | --- |
| Given Masses | 0.532 | 0.115 | 0.044 | 0.019 |
| Derived Model | 0.532 | 0.315 | 0.1 | 0.019 |

TABLE II

Anthropomorphic Model Mass Locations

| Walker parameter | Center of mass location from proximal endpoint | Calculated length (m) | Model location |
| --- | --- | --- | --- |
| Hip | 0.54 | 0 | Top of walker |
| Thigh | 0.433 | 0.2165 | From hip |
| Knee | 0 | 0.2385 | From thigh |
| Shank | 0.433 | 0.2165 | From knee |
| Foot | 0.429 | 0.2385 | From shank |

The above-described prosthetic model was used to break the assumption that the prosthetic knee location should be the same as the existing knee for transfemoral amputees. Tuning the parameters of the prosthetic model could lead to more symmetric gait patterns with reduced energy costs compared to existing prostheses. Because mass of the prosthetic limb and energy costs are proportional, it is desirable to reduce the mass of the prosthesis while moving the knee location to keep a symmetric gait pattern.

A brute force search program was used to find a lighter prosthesis. This program iterated through a range of values for the prosthetic thigh, the prosthetic shank, and the knee location. The knee location is moved by changing c1R and c2R in relation to each other. The ranges for these values can be seen in Table III. All permutations and combinations were used in the search program. Post processing was then used to analyze the large amount of data to find combinations that were optimal. The most ideal or optimal combination occurs when the mass of the prosthetic limb is reduced significantly but the gait is still stable.

TABLE III

Prosthesis Data Ranges

| Parameter | Low Value | High Value | # increments |
| --- | --- | --- | --- |
| Prosthetic Thigh | 0 | 0.1575 | 16 |
| Prosthetic Shank | 0 | 0.10 | 16 |
| Knee Location (c1R) | 0.0057 | 0.25 | 16 |

Although there are many solutions, the three different prosthesis configurations compared in Table IV will be discussed. As a baseline, the first configuration is when the knee location is in the same location as the knee of the intact leg. For this configuration to walk symmetrically the total mass of the prosthetic leg had to be increased by 2%. For this 2% leg mass increase, the thigh mass increased by 17% while the shank mass decreased by 38%. The second configuration achieved a lighter symmetric prosthesis by moving the knee mass down by 36.7% of the total shank length. In doing this, the shank mass was reduced by 68% with a thigh mass increase of 7.3%. This resulted in a 13.4% reduction of the total mass of the prosthetic leg. Even though this is a small total mass reduction, the important reduction is in the shank mass, which is fairly dramatic.

TABLE IV

Prosthesis Model Mass Results

| Configuration | Thigh Mass | Shank Mass | Total Mass |
| --- | --- | --- | --- |
| Heavier Symmetric | 17% increase | 38% decrease | 2% increase |
| Lighter Symmetric | 7.3% increase | 68% decrease | 13.4% decrease |
| Lighter Asymmetric | 2% decrease | 63% decrease | 19% decrease |

Individuals who wear a prosthesis typically have an asymmetry where their prosthetic leg has a step length that is longer than their intact leg. The first two configurations have shown that this asymmetry can be minimized, but the third configuration demonstrates that the point of symmetry can be passed and the prosthetic leg can produce a shorter step length than the intact leg. This implies that the prosthetic leg is overcompensating for the asymmetry that the wearer is likely to develop. To get this step-length outcome, the knee was moved down by 42.8%, which caused the prosthetic shank mass to be reduced by 63% and the prosthetic thigh mass to be reduced by 2%. This reduced the entire prosthetic leg mass by 19%. Once again the previous percentages are shown in Table IV. By moving the knee down and reducing the masses, the step length of the prosthesis was 7.4% less than the step length of the intact leg. This outcome shows that a prosthesis can be tuned to be lighter than the intact leg while overcompensating for the wearer's developed asymmetry.

Figure 8:
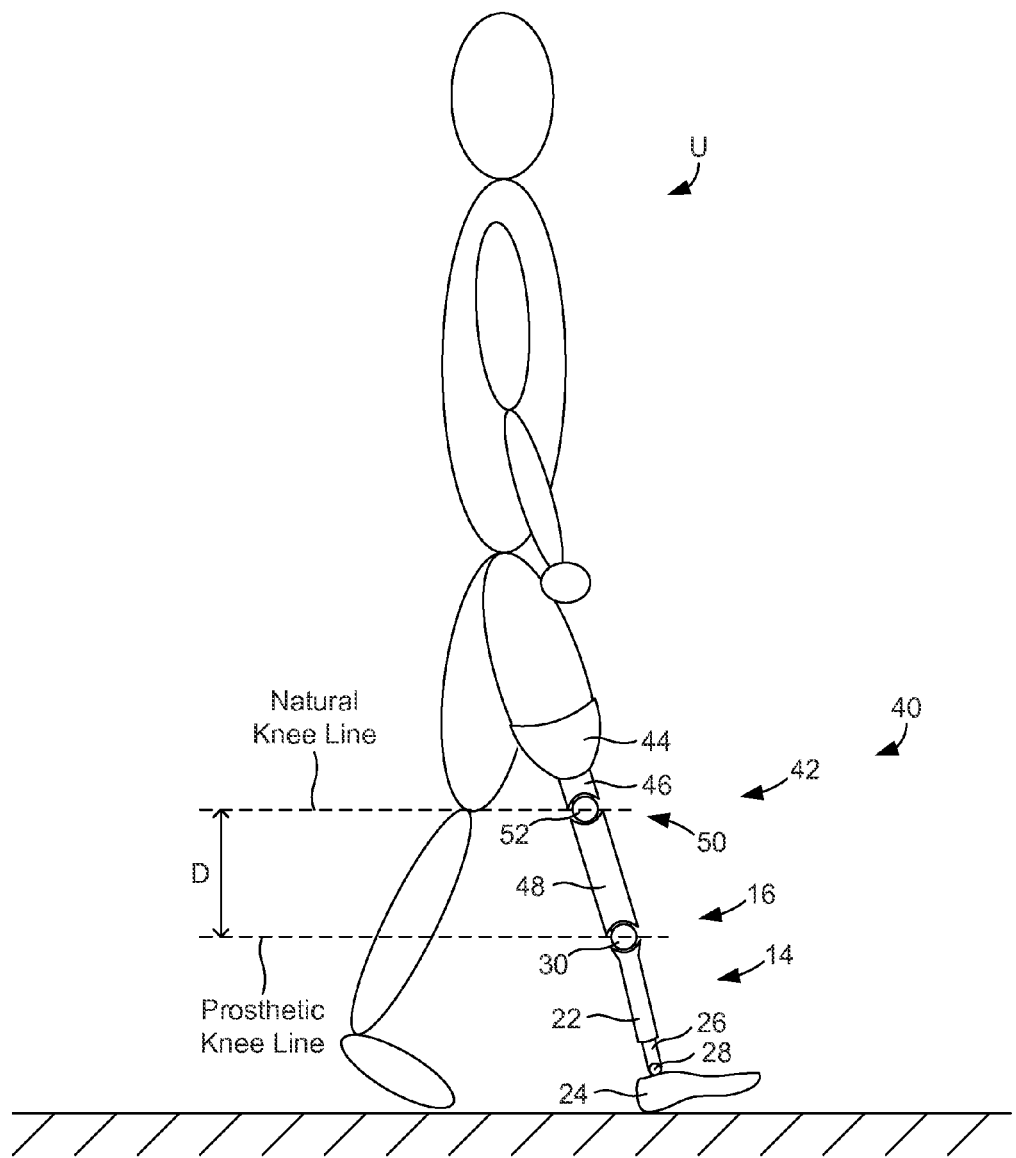
FIG. 8 is a side view of a second embodiment of a transfemoral prosthesis worn by an amputee user.

While the above-described transfemoral prosthesis design is effective at improving a transfemoral amputee's gait, the displaced location of the knee joint can be inconvenient in some situations. For example, if the user is going to sit down, the prosthesis can be awkward or can have an unnatural appearance. To alleviate such issues, the transfemoral prosthesis can have a further "knee" joint positioned at the natural knee line. An example of such an embodiment is shown in FIG. 8. FIG. 8 illustrates a second transfemoral prosthesis 40 that is similar in many ways to the prosthesis 10 of FIG. 1. Accordingly, the prosthesis 40 generally comprises an upper portion 42, a lower portion 14, and a knee joint 16 that pivotally connects the lower portion to the upper portion. The upper portion 42 includes a thigh interface 44 that is adapted to receive and attach to the remaining portion of the user's thigh. However, the shaft of the upper portion 42 actually comprises two shafts 46 and 48 that are pivotally connected by a second knee joint 50. In some embodiments, the knee joint 50 comprises a simple hinge 52 that enables pivoting about a single axis. Unlike the first knee joint 16, the second knee joint 50 is positioned at the user's natural knee line. In some embodiments, both knee joints 16, 50 can be selectively locked by the user U. In the case of the first knee joint 16, locking fixes the relative orientations of the upper portion 42 and the lower portion 14 of the prosthesis 40. In the case of the second knee joint 50, locking fixes the orientation of the upper portion 42 (i.e., the relative orientations of the shafts 46 and 48).

With this construction, the transfemoral prosthesis 40 is useful to both improve gait and facilitate natural sitting. When the user U is walking, the second knee joint 50 can be locked so that the prosthesis 40 can be operated in similar manner to that described above in relation to the prosthesis 10. When the user U wishes to sit, however, the second knee joint 50 can be unlocked and the first knee joint 16 can be locked to enable the user U to sit in a natural manner. In view of this functionality, the first knee joint 16 can be considered to be the walking knee joint and the second knee joint 50 can be considered to be the sitting knee joint.

Figure 9:
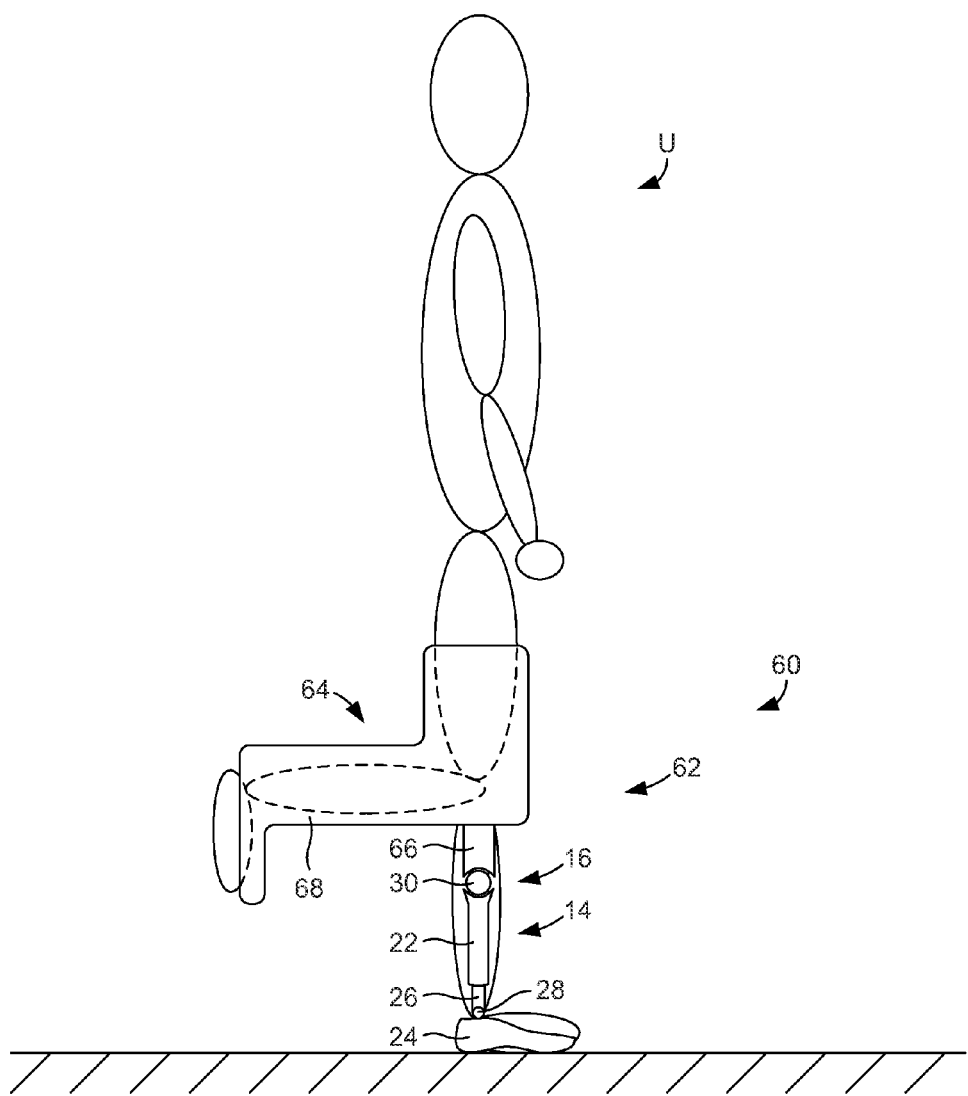
FIG. 9 is a side view of an embodiment of a body support prosthesis that can be used by non-amputees.

It is noted that the principles of the above-described transfemoral prostheses can be applied to body supports that can be used by non-amputees to facilitate walking FIG. 9 illustrates an example body support prosthesis 60 that is useful to persons with lower leg, ankle, or foot injuries. Like the above-described transfemoral prostheses, the body support prosthesis 60 generally comprises an upper portion 62, a lower portion 14, and a knee joint 16 that pivotally connects the lower portion to the upper portion. The lower portion 14 includes a shaft 22 and a foot prosthesis 24, and the foot prosthesis is connected to the shaft with another shaft 26 that includes a joint 28 that enables the foot prosthesis to pivot relative to both shafts 22 and 26.

The upper portion 62 includes a leg interface 64 and a shaft 66 that extends downward from the thigh interface to the knee joint 16. Because the body support prosthesis 60 is intended for non-amputees, however, the leg interface 64 is adapted to support the user's intact leg. More particularly, the interface 64 is adapted to support the leg while the leg is in a bent orientation. In some embodiments, the leg is bent approximately 90°. To support the leg while in such an orientation, the interface 64 generally includes a horizontal platform 68 that is adapted to support the user's knee and shin.

As with the other illustrated prostheses, the knee joint 16 of the body support prosthesis 60 is displaced downward from the user's natural knee line and can, for example, comprise a simple hinge 30 that enables pivoting about a single axis.

The body support prosthesis 60 can be used to facilitate walking without requiring the user U to put weight on the lower leg, ankle, or foot and without requiring the use of crutches. Instead of using his or her own knee joint, ambulation can be achieved by bending the knee joint 16 of the prosthesis 60. While the prosthesis 60 is particularly well suited for injured persons, it can also be used by others to provide a greater understanding of what is it like to be an amputee.

The invention claimed is:

1. A prosthesis comprising:
an upper portion adapted to interface with a user's leg;
a lower portion adapted to interface with a floor or ground surface; and
a knee joint that pivotally connects the lower portion to the upper portion, wherein the knee joint is physically displaced from the user's natural knee line along the leg when the prosthesis is properly sized and worn by the user.

2. The prosthesis of claim 1, wherein a center of the knee joint is displaced downward from the user's natural knee line.

3. The prosthesis of claim 2, wherein the knee joint is shifted downward from the natural knee line a distance that is approximately 10 to 60% of the length of the user's missing lower leg.

4. The prosthesis of claim 2, wherein the knee joint is shifted downward from the natural knee line a distance that is approximately 20 to 50% of the length of the user's missing lower leg.

5. The prosthesis of claim 2, wherein the knee joint is shifted downward from the natural knee line a distance that is approximately 30 to 40% of the length of the user's missing lower leg.

6. The prosthesis of claim 2, wherein the knee joint is positioned approximately 3 to 7 inches below the natural knee line.

7. The prosthesis of claim 1, wherein the upper portion includes a leg interface and a shaft that extends downward from the leg interface.

8. The prosthesis of claim 7, wherein the prosthesis is a transfemoral prosthesis and wherein the leg interface is a thigh interface that is adapted to interface with a partially amputated thigh of the user.

9. The prosthesis of claim 7, wherein the prosthesis is a body support prosthesis and wherein the leg interface includes a platform that is adapted to support a knee and shin of the user.

10. The prosthesis of claim 1, wherein the upper portion comprises a second knee joint.

11. The prosthesis of claim 10, wherein the second knee joint is lockable such that the orientation of the upper portion can be fixed.

12. The prosthesis of claim 1, wherein the lower portion includes a shaft and a foot prosthesis pivotally connected to the shaft.

13. The prosthesis of claim 1, wherein the location of the knee joint is fixed and its position cannot be adjusted along a length of the prosthesis.

14. The prosthesis of claim 1, wherein the knee joint is a simple hinge that pivots about a single axis.

* * * * *